United States Patent
Delanghe et al.

(10) Patent No.: US 6,774,264 B2
(45) Date of Patent: Aug. 10, 2004

(54) CATALYST TO IMPROVE THE COLOR STABILITY OF N,N-DIALKYLALKANOLAMINES

(75) Inventors: Nathalie Cecile Delanghe, Orefield, PA (US); Gamini Ananda Vedage, Bethlehem, PA (US); Frederick Carl Wilhelm, Zionsville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 69 days.

(21) Appl. No.: 10/313,560

(22) Filed: Dec. 6, 2002

(65) Prior Publication Data

US 2004/0110988 A1 Jun. 10, 2004

(51) Int. Cl.$^7$ .............................................. C07C 209/84
(52) U.S. Cl. ..................................................... 564/497
(58) Field of Search ......................................... 564/497

(56) References Cited

U.S. PATENT DOCUMENTS

| | | | |
|---|---|---|---|
| 3,207,790 A | 9/1965 | Glew et al. ................. | 260/584 |
| 3,819,710 A | 6/1974 | Jordan ........................ | 260/584 |
| 5,847,221 A | 12/1998 | Gibson ........................ | 564/498 |
| 6,291,715 B1 | 9/2001 | Ruider et al. ................ | 564/497 |

FOREIGN PATENT DOCUMENTS

| | | | |
|---|---|---|---|
| EP | 0028555 | 6/1988 | ........... C07C/89/04 |
| JP | 1160947 | 6/1989 | ........... C07C/91/06 |

*Primary Examiner*—Brian Davis
(74) *Attorney, Agent, or Firm*—Mary E. Bongiorno

(57) ABSTRACT

This invention relates to an improvement in a process for effecting decolorization of an alkanolamine by subjecting the alkanolamine to hydrogenation in the presence of a hydrogenation catalyst. The improvement for removing color, by-products, or both from a dialkylalkanolamine represented by the formula:

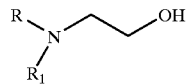

wherein R and $R_1$ are methyl, ethyl, or a mixture thereof, which comprises: utilizing a catalyst comprised of palladium carried on gamma alumina as the hydrogenation catalyst.

8 Claims, No Drawings

CATALYST TO IMPROVE THE COLOR STABILITY OF N,N-DIALKYLALKANOLAMINES

BACKGROUND OF THE INVENTION

Alkyl alkanolamines and their derivatives are widely used in the chemical industry. N,N-dimethylethanolamine (DMEA), N-methyl, N-ethylethanolamine and N,N-diethylethanolamine are representative dialkylalkanolamines which have multiple uses; for example, they are used in the production of pharmaceutical products; paints and coatings; textile auxiliaries; corrosion inhibitors; dyestuffs; and as curing agents for epoxy and polyamide resins. A specific pharmaceutical use for N,N-dimethylethanolamine is in the synthesis of procaine, a valuable local anesthetic and as an intermediate in the preparation of procaine penicillin G, an important antibiotic. N,N-dimethylethanolamine and N-methylethanolamine are also used in the synthesis of antihistamines (e.g. diphenylhydramine hydrochloride) for the symptomatic relief of allergies, such as hay fever as well as the common cold.

Currently N,N-dimethylethanolamine is mainly used in the manufacture of functional acrylate or methacrylates monomers. These monomers and their quaternized derivatives are widely used in the production of cationic polyacrylamides and other polymers for water treatment and paper making.

A known problem of alkanolamines, in general, and the dialkylalkanolamines, in particular, is that following fractional distillation of the alkanolamine crude reaction product they either are or become discolored. The sources of this color contamination may be from metals and metal compounds leached from the equipment used in the process of manufacture, or from conjugated and carbonyl containing organic compounds which are formed during the manufacturing process. Since the mechanism by which these color contaminants are formed varies from process to process and, also, from product to product, the successful decolorization process depends to a certain degree on the color source and contaminating by-product. Decolorization processes for some alkanolamines are not necessarily suited for others.

There have been many processes suggested for removing color from alkanolamines. One method commonly employed is hydrogenation. But, these hydrogenation processes also differ in terms of the process and product employed. Representative patents and articles illustrating hydrogenation processes for the decolorization of alkanolamines and the catalytic metals used therefor are as follows:

U.S. Pat. No. 6,291,715 B1 (2001) discloses the preparation of alkanolamines with improved color stability by treating the alkanolamine with hydrogen in the presence of a hydrogenation catalyst at elevated temperature. The catalysts include the metals Re, Ru, Rh, Os, Pd, Ir, Pt and Ag. These metals are carried on the supports alpha-aluminum oxide, zirconium oxide, titanium dioxide, and activated carbon. Pd on γ-alumina was used to decolorize triethanolamine but the reaction product turned pink.

JP 01-160,947 (1989) describes the purification of dialkylaminoethanols by the steps (a) removal of high boiling compounds, (b) treatment with hydrogen in the presence of hydrogenation catalyst, e.g., 5%Ru/C and (c) distillation.

EP 028,555 B1 (1988) teaches a process for the purification of N,N-dialkylaminoethanols by catalytic hydrogenation in heterogeneous phase wherein the catalyst contains a metal selected from group VIII of the periodic system, such as Ni, Co, Pt, Rh or Pd. These metals are carried on various supports such as alumina, pumice, kiesulguhr, and activated carbon.

U.S. Pat. No. 3,207,790 (1965) describes a process for improving the color quality of alkanolamines by the addition of a borohydride of an alkali metal to the alkanolamine. However, the presence of an auxiliary (stabilizer) for improving the color quality of alkanolamines can be undesirable in many important areas of application.

U.S. Pat. No. 5,847,221 (1998) discloses a process for decolorizing alkanolamines and alkyleneamines by treatment with a perfluorinated ion-exchange polymer in the acid form. As acknowledged in the background, various chemicals, Impurities often enter the production processes and manifest themselves in the form of color contamination.

U.S. Pat. No. 3,819,710 (1974) describes a process for improving color and color stability of ethanolamines by hydrogenation using selected catalysts and selected catalysts conditions. Useful catalysts for the process include Raney nickel, platinum, palladium or ruthenium.

BRIEF SUMMARY OF THE INVENTION

This invention relates to an improvement in a process for effecting decolorization of an alkanolamine by subjecting the alkanolamine to hydrogenation in the presence of a hydrogenation catalyst. The improvement for removing color or by-products or both from a dialkylalkanolamine represented by the formula:

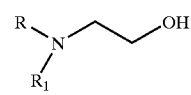

wherein R and $R_1$ are methyl, ethyl, or a mixture thereof, which comprises: utilizing a catalyst comprised of palladium carried on gamma alumina as the hydrogenation catalyst.

Significant advantages can be achieved by the process and these include:

an ability to selectively reduce some impurities critical for the main application of N,N'-dimethylethanolamine (DMEA) while obtaining a high color stability;

an ability to minimize by-product formation produced during hydrogenation; and, an ability to use a heterogeneous catalyst in the hydrogenation allowing for process advantages.

DETAILED DESCRIPTION OF THE INVENTION

The present invention is directed to an improvement in a hydrogenation process for removing color from a crude dialkylalkanolamine feedstock. The dialkylalkanolamines are represented by the formula:

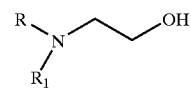

wherein R and $R_1$ are methyl, ethyl, or a mixture thereof. The preferred dialkylalkanolamine is dimethylethanolamine.

Dimethylethanolamine or as sometimes referred to as dimethylaminoethanol has been particularly difficult to treat in terms of the color or contaminants. By-product formation in the hydrogenation process has been a specific problem.

These by-products can, if present in a sufficient amount, detract from its use in many applications.

Is has been found that a catalyst comprised of palladium carried on a support of a gamma alumina having a high surface area is highly effective in the hydrogenation process. The palladium is added in an amount effective to permit hydrogenation, typically from 0.1 to 2% by weight. Preferably from about 0.3 to 0.7% by weight palladium is carried on the support, based upon the weight of the catalyst.

In contrast to many types of supports associated with the removal of color in alkanolamines, the support employed here is gamma alumina having a high surface area. Surface areas in the range from 200 to 400 m$^2$/gram are well suited.

The catalyst can be prepared by conventional techniques such as incipient wetness wherein a solution of a palladium salt is impregnated onto the surface of the support and the resulting impregnated and coated support dried and calcined. It is important in the overall hydrogenation process that metal be carried on the surface of the support. Calcination temperatures range from 300 to 600° C. and reduction temperatures can range from 300 to 500° C.

The hydrogenation process is carried out at conventional temperatures, e.g., from 100 to 160° C. and conventional hydrogenation pressures, e.g., from 1 to 10 bars. In contrast to some processes, it is preferred that the hydrogenation be conducted under substantially anhydrous conditions, e.g., less than 1% water by weight and preferably less than 0.1% by weight. In those cases where the crude alkanolamine is prepared in the presence of water, e.g., diethylethanolamine, it is highly desirable to remove the water prior to effecting hydrogenation.

The following examples are provided to illustrate various embodiments of the invention and are not intended to restrict the scope.

General Hydrogenation Procedure

Material and Methods

The apparatus employed is comprised of a DMEA feed pump, a vaporizer and a reactor. The dimethylethanolamine (DMEA) feed is pumped from a feed vessel into the base of the vaporizer. The vaporizer is constructed from stainless steel; it is electrically heated and is heavily insulated. It is packed with inert glass beads to give a uniform temperature and heat transfer across the central cavity. The vaporizer block is maintained at 160° C. during operation in order to vaporize the DMEA entering the base of the unit. Any non-vaporized residues remain coated on the packing and the walls. The vaporizer is cleaned and repacked between each trial.

Hydrogen is mixed with the DMEA vapor in the vaporizer and the mixed stream leaves through the top of the unit and passes into the oven where, prior to charging to the reactor in order to achieve thermal equilibrium.

The reactor is constructed of stainless steel with an internal diameter of 15.8 mm and is 100 mm long and filled with 13 g of catalyst and retained within the oven. After the mixed stream passes out of the reactor it is cooled. It passes through a sample loop that can be isolated from the system where a sample is taken. Then the remaining hydrogen is separated, metered, and passed to the atmosphere. The waste DMEA is collected and disposed off as amines waste. The unit pressure is controlled by a back regulator from the hydrogen line after the separator to the hydrogen feed line.

In carrying out the hydrogenation reactions, the feed rate was 50 ml/s. The reactor hydrogenation pressure was maintained at 0.5 barg, measured at the reactor exit. The reaction temperature was 135° C.–150° C.

Product samples collected from the unit were analyzed by GC using a Perkin Elmer 8420 with an auto sampler attachment and FID detector.

EXAMPLE 1

Evaluation of Palladium on Various Supports

The general procedure was followed except that various supports, i.e., activated carbon, zirconia (ZrO$_2$), magnesium oxide (MgO), calcium oxide (CaO), and gamma alumina were evaluated. The level of palladium was 0.5% on each support except where zirconia was the support and that level was 0.3% by weight. Table 1 provides the results.

TABLE 1

| Catalyst | 0.5% Pd/C | 0.5% Pd/MgO | 0.5% Pd/ZrO$_2$ | 0.3% Pd/ZrO$_2$ | 0.5% Pd/Al$_2$O$_3$ |
|---|---|---|---|---|---|
| By-products | 436 ppm | 190 ppm | 400 ppm | 215 ppm | 230 ppm |

The results show that compared to Pd/C, lower activity towards by-products formation is obtained with the catalyst consisting of Pd on the ZrO$_2$, MgO, and gamma alumina supports (Chart 1). Also, when the Pd content on the zirconia support is lower, significantly fewer by-products are formed.

Although not shown in Table 1, Pd catalysts based on zirconia and magnesium oxide supports present a very poor efficiency towards the conversion of unsaturated species (<35%) and a rapid decay in their ability to convert unsaturates, which exclude them from the selection. On the other hand 0.5%Pd/Al$_2$O$_3$ presents a high efficiency towards the conversion of unsaturated species (80%) and had a slow decay (Chart 1).

These additional properties makes it the catalyst of choice because 0.5%Pd/Al$_2$O$_3$ meets all the criteria: it improves the color stability of DMEA, it has a high activity towards the reduction of unsaturated species, it has a low activity towards the by-products formation and a slow decay.

The CaO support was disqualified because the extrudate broke down into powder during the experiment.

The results show that palladium on gamma alumina is superior to palladium on activated carbon, the conventional catalysts used in the decolorization of DMEA.

The effectiveness of gamma alumina in the hydrogenation of the respective dialkylalkanolamines is surprising in that alpha-aluminum oxide has been shown to be more effective in the treatment of triethanolamine than palladium on gamma alumina. It is also surprising that Pd on gamma alumina is successful in decolorizing the dialkylalkanolamines in view of the fact it was unsuccessful in decolorizing the trialkanolamines.

What is claimed is:

1. In a process for effecting decolorization of an alkanolamine by subjecting the alkanolamine to hydrogenation in the presence of a hydrogenation catalyst, the improvement for removing color and minimizing by-product formation or both from a dialkylalkanolamine represented by the formula:

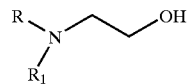

wherein R and R$_1$ are methyl, ethyl or a mixture thereof which comprises: utilizing a catalyst comprised of palladium carried on gamma alumina as the hydrogenation catalyst.

2. The process of claim 1 wherein the palladium is carried on the gamma alumina in an amount from 0.1 to 2% by weight of the catalyst.

3. The process of claim 2 wherein the hydrogenation is carried out under substantially anhydrous conditions.

4. The process of claim 3 wherein the gamma alumina has surface area of from 200 to 400 m²/gram.

5. The process of claim 4 wherein R and $R_1$ are methyl.

6. The process of claim 4 wherein the hydrogenation temperature is from 100 to 160° C. and there is less than 0.1% water present when effecting hydrogenation.

7. The process of claim 6 wherein the hydrogenation pressure is from 1 to 10 bars.

8. The process of claim 7 wherein the palladium is present in an amount of from 0.3 to 0.7% by weight of the catalyst.

* * * * *